(12) United States Patent
Levin et al.

(10) Patent No.: US 6,585,964 B1
(45) Date of Patent: Jul. 1, 2003

(54) METHOD FOR PREVENTING OR MINIMIZING BIODEGRADATION OF A SUBSTANCE

(75) Inventors: Gilbert V. Levin, Annapolis, MD (US); Roy B. Pinchot, Silver Spring, MD (US)

(73) Assignee: Biospherics Incorporated, Beltsville, MD (US)

(*) Notice: Subject to any disclaimer, the term of this patent is extended or adjusted under 35 U.S.C. 154(b) by 0 days.

(21) Appl. No.: 09/305,739

(22) Filed: May 6, 1999

(51) Int. Cl.[7] .............................. A61K 7/32; A61K 7/42; A61K 7/00; A61K 7/46; A61L 9/01
(52) U.S. Cl. .................. 424/65; 424/59; 424/76.1; 424/400; 424/401; 512/1
(58) Field of Search ....................... 424/65, 59, 401, 424/76.1; 512/1

(56) References Cited

FOREIGN PATENT DOCUMENTS

| | | | |
|---|---|---|---|
| EP | 0 884 045 A1 | * | 12/1998 |
| JP | 10120541 | * | 5/1998 |

OTHER PUBLICATIONS

The Merck Index, An Encyclopedia of Chemicals, Drugs and Biologicals, 1996, p. 896, Compound No. 5273.

* cited by examiner

*Primary Examiner*—Shelley A. Dodson
(74) *Attorney, Agent, or Firm*—Roylance, Abrams, Berdo & Goodman, L.L.P.

(57) ABSTRACT

There is disclosed a method for preventing or minimizing biodegradation of a substance which normally contains a naturally occurring optical isomer which comprises replacing the naturally occurring optical isomer with the corresponding unnatural optical isomer.

20 Claims, No Drawings

METHOD FOR PREVENTING OR MINIMIZING BIODEGRADATION OF A SUBSTANCE

BACKGROUND OF THE INVENTION

This invention relates to a method for preventing or minimizing biodegradation of a substance which normally contains a naturally occurring optical isomer. More particularly, this invention relates to a process for rendering a substance or surface supporting microorganisms, or subject to deliberate or accidental contamination with microorganisms, odoriferous, e.g., fragrant, for an extended period of time.

Next to sight, the sense of smell is reported to be that sense most widely appreciated. It plays an important role in our everyday lives. For this reason, the fragrance industry has grown to its present enormous size. Commercially sold fragrances are based on natural products and synthetic ones. The latter have become of increasing importance as the science of chemistry has become more inventive. Natural fragrances have also been synthesized. However, many of the most pleasant, or otherwise desired odors are highly transient, requiring frequent re-applications, or disappearing after periods shorter than desired for the intended uses.

Fragrant or odoriferous preparations generally consist of two functional components: the odor-producing compound or material, and a vehicle which serves as a carrier for the fragrant molecules. Such vehicles have served their purpose when the fragrance has been adequately disseminated. These vehicles are generally short-chain organic compounds which then evaporate quite quickly. This leaves the generally longer-chain fragrant molecules in situ in the desired locations from which they, in turn, volatilize, although somewhat more slowly. The sustained volatilization of these fragrant molecules achieves the desired effect by contacting the olfactories of the target persons or animals in the affected area.

While the fragrant compound applied to the site will ultimately be completely exhausted through volatilization, the full potential of this effective time is seldom, if ever, realized. This is because the fragrant molecules may be biodegradable and they are generally applied to areas rich in microorganisms. An application is to skin, which is well known to be heavily laden with microorganisms. However, all other common surfaces are also heavily populated with microorganisms. The interests of economy and personal appearance require that perfumes, for example, be applied sparingly. The biodegradability of the organic fragrance molecules results in the microbial populations attacking these molecules, metabolizing them and rendering the remains non-fragrant, less fragrant, or even of an undesirable odor. The otherwise expected useful time of the application of the product is thus effectively reduced.

In recent years, there has been a continuing replacement of natural fragrances with chemically synthesized molecules. Some are identical to natural fragrances, but are made synthetically more cheaply than can otherwise be obtained. Others are novel compounds, but these are also generally biodegradable. Both types of products suffer the same fate as described above for the natural fragrances.

SUMMARY OF THE INVENTION

In accordance with this invention, there is provided a method for preventing or minimizing biodegradation of a substance which normally contains a naturally occurring optical isomer, which process comprises replacing the naturally occurring optical isomer with the corresponding unnatural optical isomer. Examples of such substances include fragrances, substances which contain fragrances, and nonfragrant substances which contain optical isomer(s), such as body lotions, soaps, deodorants, and dyes and paints.

In a preferred embodiment of this invention, there is provided a process for prolonging emanation of odor(s) from a substance or surface containing one or more odoriferous optically isomeric compounds and which substance or surface also contains or becomes contaminated with microorganisms, which process comprises selecting (an) unnatural optical isomer(s) of the compound(s) to prevent or delay biodegradation of the odoriferous compound(s).

More particularly, it has now been found that an odoriferous compound applied to a substance or surface such as skin, may render the desired odor for an extended period of time by selecting its non-naturally occurring optical stereoisomer for use on the surface. The resulting substance or surface will remain odoriferous for a longer period of time than if the naturally occurring optical stereoisomer had been applied. This is because the non-naturally occurring optical stereoisomer is non-biodegradable, or is of greatly reduced biodegradability since the microbial enzymes necessary to the biodegradation process can cope only with the naturally occurring optical stereoisomer.

DETAILED DESCRIPTION OF THE INVENTION

Some of the organic molecules synthesized for fragrance purposes, and some of the natural fragrance molecules which can be synthesized have structures which contain carbon atoms bonded to four different atomic groups. The four atomic groups can assume one of two opposite configurations about their central carbon atom. For the purpose of chemical reactions, these configurations behave identically. Although little used as fragrances, amino acids and carbohydrates are important examples of chirality, the occurrence of optical stereoisomers of the same molecule, and serve to illustrate the point. Virtually all amino acids in nature are of the optically stereoisomeric form designated "left handed", while natural carbohydrates occur almost exclusively in the optically stereoisomeric form called "right handed". (These common designations derive from their mirror images which demonstrate the chemical identity, but not superimposability of the two forms of the same molecule.) The reason for the natural preference of one optical stereoisomer over its opposite form is unknown, but all known life forms follow this preference in their consumption and production of chiral organic compounds.

Some natural chemicals used in perfumery, and which have optical isomers, are listed in Table 1.

TABLE 1

Some Fragrances and their optical Isomers

| NATURAL OPTICAL ISOMER | UNNATURAL OPTICAL ISOMER |
| --- | --- |
| (1R,2S,5R)-(−)-Menthol | (1S,2R,5S)-(+)-Menthol |
| (R)-(+)-Citronellal | (S)-(−)-Citronellal |
| (−)-Linalool | (+)-Linalool |
| (−)-Menthone | Four isomers |
| (1R)-(−)-Menthyl Acetate | (1S)-(+)-Menthyl Acetate |

The strong preference, or specificity, for natural optical isomers displayed by biological entities is because virtually all biological reactions are conducted through the participation of enzymes. From the time life originated, its first enzymes have consistently passed on their optical isomeric specificity to all life forms evolved down through the eons. Enzymes, being templates which position molecules for specific reactions, do distinguish between, or among, optical isomers of the same molecule. Not being able to fit physically to the other optical isomer of the reactive molecular species, an enzyme cannot induce the reaction with the unnatural optical isomer.

The sense of smell has been attributed to enzymatic reactions: "Olfactory transduction begins with the binding of an odorant ligand to a protein receptor of the olfactory neuron cell surface, initiating a cascade of enzymatic reactions . . . "(Breer, H., *Semin. Cell Biol* 5, 25, 1994; Sheppard, G. M., *Neuron* 13, 771, 1994, cited by Zhao, H. et al, *Science*, 279, 237, 1998). A fundamental characteristic of enzymatic reactions is their specificity for the molecule they catalyze into reaction. "Perhaps the most striking aspect of the specificity of enzymes is their ability to select between enantiomorphous compounds. This may be termed stereochemical specificity. For example, carboxypeptidase, which catalyzes the hydrolysis of carbobenzoxyglycyl-L-phenalalanine, has no measurable action on carbobenzoxyglycyl-D-phenalalanine. . . . These examples of stereochemical specificity involve an absolute discrimination between enantiomorphs." (General Biochemistry, Fruton and Simmonds, eds, 3rd printing, p. 277, John Wiley & Sons, Inc., N.Y., 1960). A number of fragrant or odoriferous compounds are natural optical isomers. It would be expected that the unnatural enantiomers of these compounds would not trigger the sense of smell, because their molecules would not fit the protein (enzyme) receptor encountered. Since the enzyme receptors have evolved to fit with natural products only, the unnatural optical isomer would not fit, and, therefore, no odor-sensing reaction would be expected to occur with the neuron. However, it has been found that both the naturally occurring optical stereoisomer and the non-naturally occurring optical stereoisomer have the same odor.

The odoriferous compounds used in the practice of this invention may be used in perfumes, eau de colognes, powders, mouth washes, dentifrices, confections, deodorants for personal and area uses, douches, hair applications, simulated odors for various products (such as leather odors for plastic upholstery), tobacco products, insect and animal repellants and attractants, and the wide variety of other products and uses for fragrances, masking odors, artificial odors, or other scents including those used in foodstuffs, beverages and the like.

EXAMPLE 1

The naturally-occurring optical isomer of menthol (1R, 2S,5R)–(–) is used as a fragrance in a variety of products, such as perfumes, gums, and cigarettes. Both the natural and the unnatural (1S,2R,5S)–(+) optical isomer of menthol were obtained in 99% purity. A 0.001M solution of each enantiomer was prepared in reagent grade acetone. The solutions were allowed to equilibrate at room temperature for approximately one hour. Twenty drops of each solution were pipetted into separate glass Petri dishes. All glassware was clean. The acetone was then allowed to evaporate at room temperature. A human subject then smelled the two Petri dishes separately and recorded any sensations. The subject had been instructed to determine the presence of odor in the Petri dishes, and, if odor emanated from each, to determine whether the odors were the same or different. The test was performed twice on each of six human subjects, three female and three male. Each subject was given freshly prepared Petri dish servings to smell, and each immediately recorded his or hers impressions without communicating with the other subjects.

All six subjects found that the unnatural form of menthol had odor. Moreover, all six found the odor of the unnatural form to be the same as that of the natural form. These results may constitute evidence that the sense of smell is not enzymatic as heretofore accepted by the scientific community.

What is claimed is:

1. A process for prolonging emanation of odor from a substance or surface containing one or more odoriferous optically isomeric compounds which process comprises selecting an unnatural optical isomer of the compound(s) for use in or on the substance or surface to prevent or delay biodegradation of the fragrance by microorganisms present on, or accidentally or deliberately contacting the substance or surface.

2. A process for rendering a substance or surface odoriferous for an extended period of time which comprises selecting an odoriferous compound which can exist in the form of optical stereoisomers, one being naturally occurring and the other being non-naturally occurring and applying to said substance or surface said non-naturally occurring optical stereoisomer to prevent or delay biodegradation of the odoriferous compound.

3. A process according to claim 2 wherein said surface is human skin, hair or mucosal tissue.

4. A process according to claim 2 wherein said odoriferous compound is a fragrance.

5. A process according to claim 2 in which the substance incorporating the odoriferous compound are selected from the group consisting of perfumes, eau de colognes, powders, mouth washes, dentrifices, confections, deodorants for personal and area uses, incenses, candles, shaving creams and lotions, body lotions, shampoos, laundry and dry cleaning products, dish cleansers, furniture and leather treatments, douches, hair applications, simulated odors for various products, tobacco products, household and personal cleansers, insect and animal repellents and attractants, foodstuffs, and alcoholic and non-alcoholic beverages.

6. An odoriferous product obtained by the process of claim 1.

7. An odoriferous product obtained by the process of claim 2.

8. An odoriferous product obtained by the process of claim 3.

9. An odoriferous product obtained by the process of claim 4.

10. An odoriferous product obtained by the process of claim 5.

11. An odoriferous product obtained by the process of claim 6.

12. An odoriferous product obtained by the process of claim 7.

13. An odoriferous product obtained by the process of claim 8.

14. A process for rendering a substance or surface odoriferous for an extended period of time which comprises selecting an odoriferous compound which can exist in the form of optical stereoisomers, one being naturally occurring and the other being non-naturally occurring and applying to said substance or surface said non-naturally occurring optical stereoisomer to prevent or delay biodegradation of the odoriferous compound, wherein said odoriferous compound is a member selected from the group consisting of menthol, citronellal, linalool, menthone and menthyl acetate.

15. A process according to claim 14 wherein said odoriferous compound is (1S, 2R, 5S)-(+)-menthol.

16. A process according to claim 14 wherein said odoriferous compound is (S)-(−)-citronellal.

17. A process according to claim 14 wherein said odoriferous compound is (+)-linalool.

18. A process according to claim 14 wherein said odoriferous compound is menthone.

19. A process according to claim 14 wherein said odoriferous compound is (1S)-(+)-menthyl acetate.

20. An odoriferous product obtained by the process of claim 14.

\* \* \* \* \*